United States Patent [19]

Nakamura et al.

[11] Patent Number: 4,716,907
[45] Date of Patent: Jan. 5, 1988

[54] APPARATUS FOR DETECTING ELECTROENCEPHALOGRAM AND EVOKED RESPONSE WITH MONOPOLAR DERIVATION METHOD

[75] Inventors: Masatoshi Nakamura, 12-30, Onimaru-cho; Hiroshi Shibasaki, No. 625 Idai-shukusha, 3-10 Yaemizo, both of Saga-shi, Saga-ken; Shigeto Nishida, Saga, all of Japan

[73] Assignees: Hiroshi Shibasaki; Masatoshi Nakamura, both of Saga, Japan

[21] Appl. No.: 898,698

[22] Filed: Aug. 21, 1986

[30] Foreign Application Priority Data

Aug. 23, 1985 [JP] Japan .................................. 60-186441
Aug. 23, 1985 [JP] Japan .................................. 60-186442

[51] Int. Cl.$^4$ ............................................... A61B 5/04
[52] U.S. Cl. .................................................... 128/731
[58] Field of Search ................. 128/731, 732; 364/417

[56] References Cited

U.S. PATENT DOCUMENTS 4,308,873 1/1982 Maynard .............................. 128/731
4,421,121 12/1983 Whisler et al. ....................... 128/731

Primary Examiner—Lee S. Cohen
Attorney, Agent, or Firm—Hoffmann & Baron

[57] ABSTRACT

An electroencephalogram (EEG) and an electrocardiogram (EKG) signal are detected, and said EEG signal is divided into segments in synchronization with said EKG signal, whereby said segmented EEG signals are averaged. EKG-originating noises yielded as such are subtracted from the EEG signal, whereby an actual EEG signal is derived. The resultant actual EEG signal is divided into segments in synchronization with a stimulation signal, and the segmented actual EEG signals are averaged for enhancing an evoked response signal.

9 Claims, 9 Drawing Figures

APPARATUS FOR DETECTING ELECTROENCEPHALOGRAM AND EVOKED RESPONSE WITH MONOPOLAR DERIVATION METHOD

BACKGROUND OF THE INVENTION

The present invention relates to a device for detecting an electroencephalogram (EEG) and evoked response by making use of a method of monopolar derivation wherein one electrode is attached to the scalp and the other electrode mounted on a body portion other than the scalp.

According to the monopolar derivation method, a reference electrode is attached in general at a head location such as on an earlobe, the nose, the jaw, and the like. However, such a reference electrode causes some troubles to an interpretation of the result since it is sometimes activated by EEG or evoked response. To solve this problem the reference electrode is often mounted on a body portion other than a head location, whereas there arises another problem that the noise produced due to an electrocardiograph (EKG) and mixed into EEG as artifacts increases.

U.S. Pat. No. 4,421,121 is known as providing an EEG detector-unit capable of eliminating the noise caused by the EKG, wherein an EKG signal is detected by another pair of electrodes and then is subtracted from an EEG under the correlation of the amplitude with each other. However, it is difficult to eliminate with high accuracy such noises involved in the EEG because the EKG different from one mixed into the EEG is used for cancellation.

In addition, here is another problem, also upon detecting an evoked response to a stimulation, namely, an evoked response being masked with EKG noises as well as being barried in a background EEG owing to use of the monopolar derivation method. Thereupon, a method is known of eliminating the background EEG by averaging the evoked response signal in synchronization with the stimulation, but it is again difficult to eliminate noises produced due to an EKG which mixes at a high level into the EEG signal in concern.

SUMMARY OF THE INVENTION

In view of the drawbacks of the prior EEG apparatus, it is an object of the present invention to provide an EEG detecting apparatus capable of eliminating with accuracy noises involved in an EEG, the noises being produced due to an EKG which mixes at a high level into an EEG signal.

Another object of the present invention is to provide an evoked response detecting apparatus capable of eliminating with high accuracy noises involved in due evoked response, the noises being produced due to an EKG which mixes at a high level into the evoked response signal.

To achieve the above objects, the present invention is adapted to derive an EEG signal and an EKG signal at the same time, divide the EEG into segments synchronized with the EKG signal, render the EEG signals of the respective segments to averaging in synchronization with the EKG signal to evaluate noises in the EEG, and subtract the noises produced due to the EKG from the EEG.

The noises in the EEG produced due to the EKG are hereby evaluated for cancellation, and hence an actual EEG signal can be derived highly accurately. Namely, since a reference electrode can be mounted on a patient body location such as the 1aw, a hand, a food, etc., other than his scalp without any trouble, an EEG derived from an exploring electrode on the scalp can be detected highly accurately.

Upon detecting the evoked response signal, an actual EEG from which noises produced due to an EKG have already been eliminated in conformity with the processing described above is divided into segments in synchronization with a period of a stimulation signal, and the actual EEG signal of each segment is subjected to averaging in synchronization with the stimulation signal to enhance the evoked response signal. Namely, the noise produced due to the EKG is eliminated by the first processing step of averaging and subtraction, and then a background EEG is eliminated by the second processing step of averaging.

The above and other objects, features and advantages of the present invention will become more apparent from the following description when taken in conjunction with the accompanying drawings in which a preferred embodiment of the present invention is shown by way of illustrative example.

DESCRIPTION OF THE PREFERRED EMBODIMENT

Referring now to the accompanying drawings, arrangement and operation of an apparatus for detecting an EEG and an evoked response according to the present invention will be described.

Figure 1:
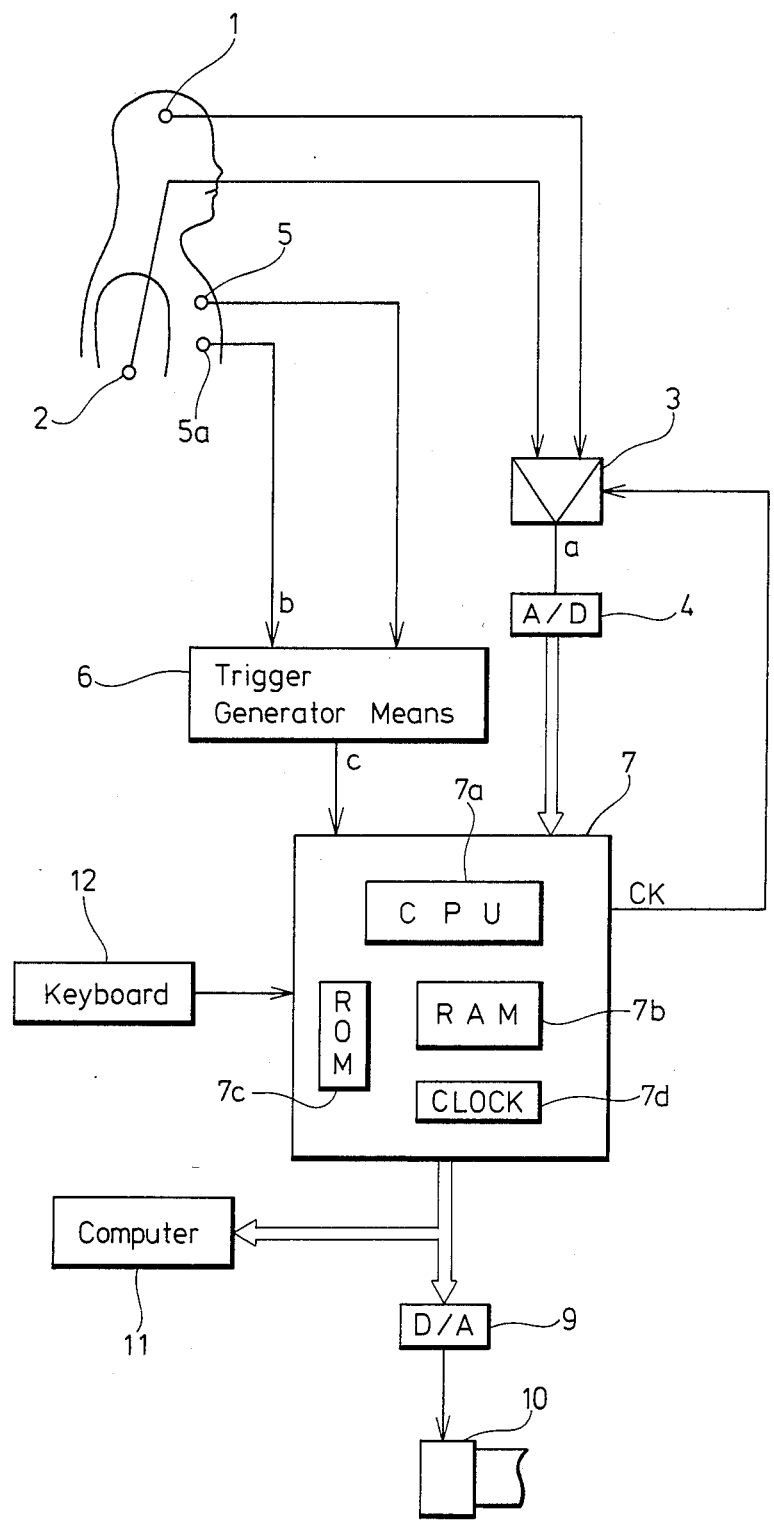
FIG. 1 is a circuit block diagram illustrating an embodiment of an apparatus for detecting an EEG and an evoked response signal according to the present invention.
Figure 2:
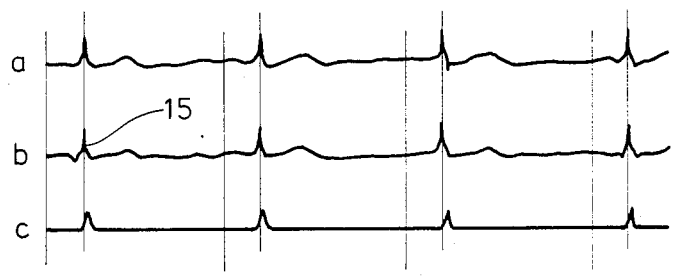
FIGS. 2 to 5 are respectively illustrations of an operation waveform at each portion.

As shown in FIG. 1 illustrating the apparatus for detecting an EEG and an evoked response of the present invention, designated at 3 is an amplifier having as an input thereto potential derived between a scalp electrode 1 and an electrode 2 attached to a body part other than the head, for example a hand, and the amplifier outputs an amplified EEG signal (a) (refer to FIG. 2). Designated at 4 is an A/D converter for digitizing the EEG signal (a) in a sampling interval of 1 ms with a resolution of 12 bits in synchronization with a clock signal CK. Designated at 6 is a trigger generator circuit for generating a trigger (c) (FIG. 2) based on R waves 15 having a maximum peak in an EKG signal (b) (FIG. 2) taking as an input the EKG signal (b) derived from electrodes 5, 5a attached to another body portion, for example to the chest, the trigger generator circuit being composed of a Schmidt trigger circuit serving to level-descriminate the R waves 15 and a differentiation circuit for an output from the Schmidt circuit.

Figure 3:
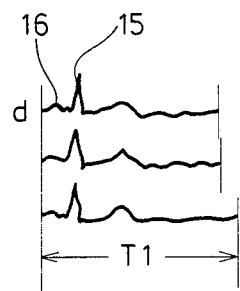

Designated likewise at 7 is a microcomputer employed as averager means for averaging a digitized EEG signal (a) in synchronization with a trigger signal (c) as well as substractor means for subtracting the averaged signal from the EEG signal (a), the microcomputer being as well known composed of a CPU 7a, a RAM 7b, a ROM 7c, and a clock generator 7d. The CPU 7a is operated in synchronization with a clock signal available from the clock generator 7d in confomity with a program stored in the ROM 7c and temporarily storing the digitized EEG signal (a) in the RAM 7b in succession at an address thereof corresponding to the elapse of time. In addition, the CPU 7a divides as shown in FIG. 3 the EEG signal (a) into a segment T1 corresponding to a period of the EKG signal so as to start the segment from an address corresponding to a time going back to the past from a reference address corresponding to the time the trigger signal (c) is generated. The CPU 7a then averages the segmented EEG signal (d) shown in FIG. 3 on the basis of the following formula for evaluating a noise signal:

$$Zm(k) = [1 - 1/m]Zm - 1(k) + [1/m]Ym(t)$$

where,

Zm (k): a noise signal subjected to [m] times of averaging, and

Ym (t): a segmented EEG signal.

Figure 4:

Namely, at the time of the averaging of [m] times the present noise signal $Zm-1$ (k) averaged as such is first multiplied by $[1-1/m]$, and then a segmented EEG signal Ym (t) incorporated anew is multiplied by $[1/m]$, and finally both are added. The noise signal Zm (k) so averaged corresponds to an EKG-originating noise (e) shown in FIG. 4. The CPU 7a computes the successive subtraction of the averaged noise signal Zm (k) from the segmented EEG signal Ym (t) for evaluating an actual EEG signal Xm (t) on the basis of $Xm(t) = Ym(t) - Zm(k)$.

When the averaging number [m] reaches to a certain large value [M], it is also possible to evaluate the noise signal Zm (k) by fixing the coefficients $[1-1/m]$ and $[1/m]$ respectively to $[1-1/M]$ and $(1/M)$. In addition, with such arithmetic operation as described above, even if the EKG-originating noise such as arrhythmia, etc., different in its nature from the above-described EKG-originating noises is abruptly produced after the averaging is effected by M times, a segmented EEG signal Ym (t) at that time is multiplied by the constant coefficient, 1/M and incorporated into the noise signal Zm (k). Accordingly, an influence of the EKG-originating noise abruptly produced as such on the EEG signal can be reduced for assuring a more accurate operation result. A predetermined time preceding the trigger (c) is set to for example 200 ms so as to correspond to a time interval where a P wave 16 preceding the trigger (c), i.e., an R wave 15 is existent.

Designated at 10 is a recorder for recording the actual EEG signal Xm (t) supplied in succession by an analog signal with use of a D/A converter 9. Designated at 11 is a diagnostic computer to be successively supplied with the actual EEG signal Xm (t) for diagnosis based on a database included therein, and 12 is a keyboard for performing the setting of the predetermined time preceding the trigger (c) described above and other required operations in accordance with patients.

Operating of the apparatus for detecting an EEG signal arranged as such will be described.

Figure 5:
Figure 6:
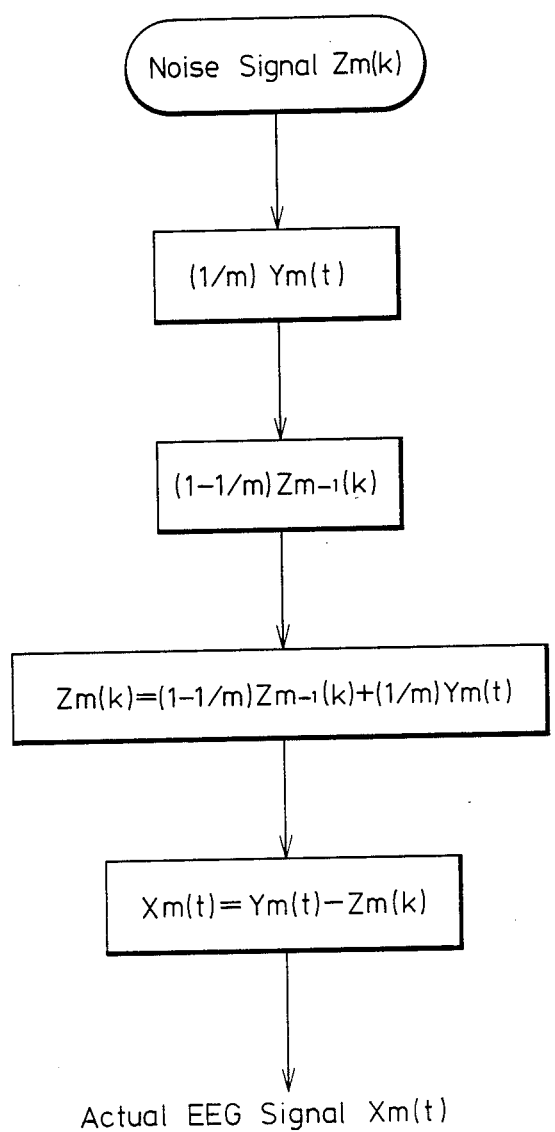
FIG. 6 is a flowchart illustrating operation of a microcomputer included in the present invention.

A potential derived on the electrodes 1 and 2 is amplified for its detection through the amplifier 3 as an EEG signal (a) and digitized in the A/D converter 4. The trigger signal generator means 6 issues a trigger signal (c) based on an EKG signal (b) detected on the electrodes 5, 5a. The microcomputer 7 receives the EEG signal (a) so digitized successively, and subjects in succession respective segmented EEG signal Ym (t) starting from a time going back to the past by 200 ms taking the trigger (c) as a reference to averaging and subtraction in conformity with FIG. 6 to deliver an actual EEG signal Xm (t). Hereby, in the recorder 10, a pure actual EEG signal (f) wherefrom the EKG-originating noise has been eliminated as shown in FIG. 5 is drawn in real time delayed by 200 ms. The diagnostic computer 11 is possible to carry out highly accurate diagnosis in an on-line or off-line mode.

Moreover, in the above embodiment, the EKG signal (b) being an input to the trigger generator means 6 is derived from the electrodes 5, 5a attached to the chest of a patient, but it may also be allowed to separate and extract an EKG signal mixed in the EEG signal derived from the electrodes 1, 2 via an R wave detector circuit serving as a band-pass filter. In addition, the trigger generator means can also be adapted to issue a trigger at the time of a digital value yielded by digitizing an EKG signal entered in succession exceeding a level for detecting the R waves. Furthermore, it may also be possible to use a plurality of electrodes as the electrode attached to the scalp for scanning EEG signals on a plurality of channels with those electrodes at a high speed and further evaluating those signals with use of the microcomputer 7.

Figure 7:
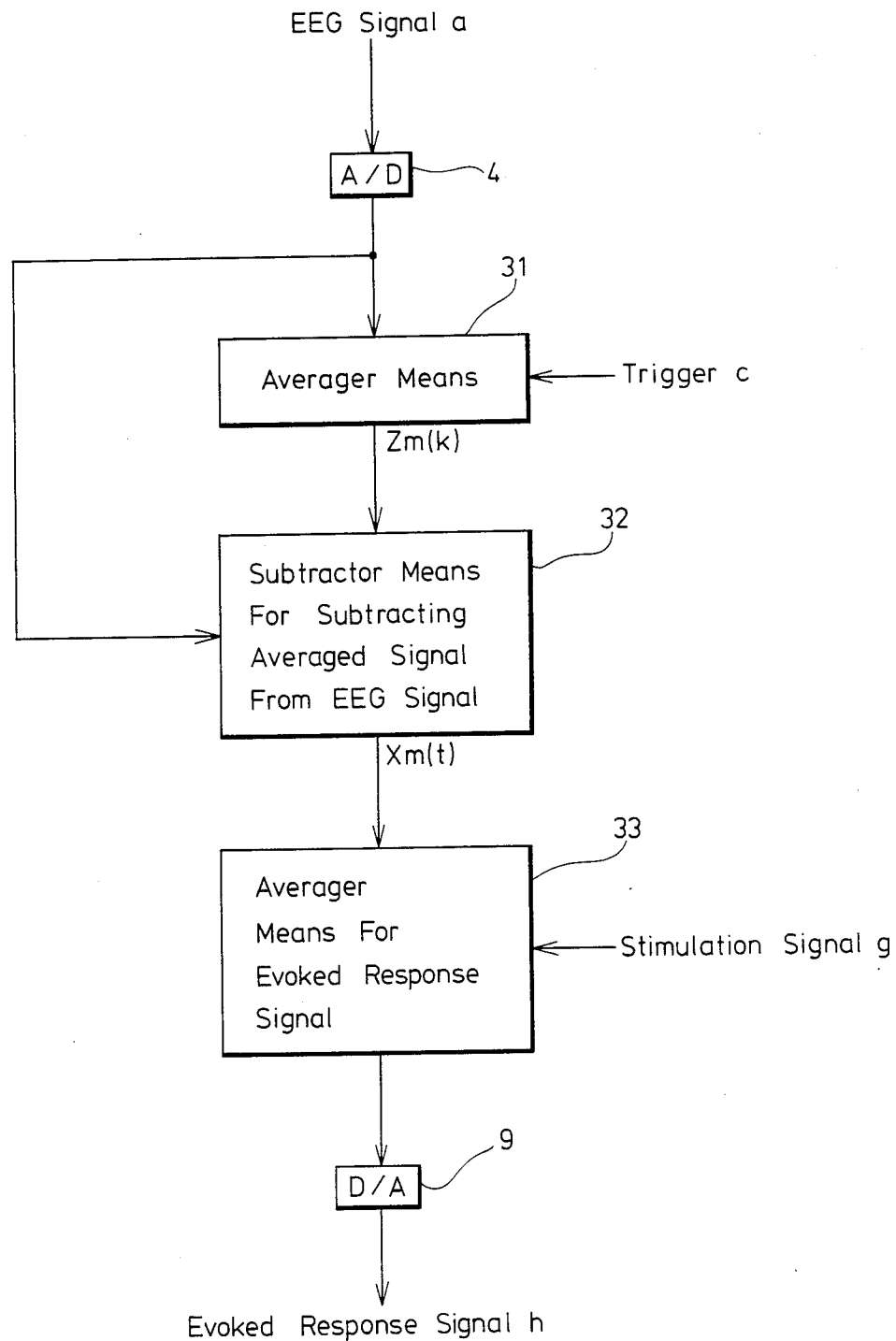
FIG. 7 is a circuit block diagram illustrating another embodiment of the present invention.
Figure 8:
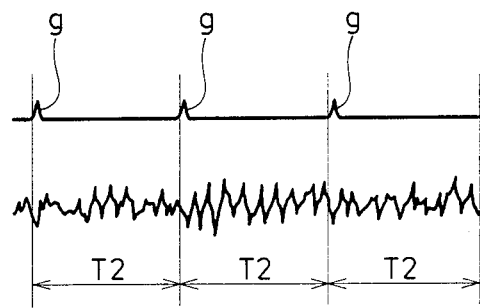
FIGS. 8 and 9 are respectively illustrations of an operation waveform of each part of FIG. 7.

Referring here to FIG. 7, a block diagram is shown illustrating arrangement of an arithmetic operation part of another embodiment of the evoked response detecting apparatus for detecting an evoked response signal produced as a result of subjecting a patient to external stimulation such as light, sounds, electric pulse, etc. The arithmetic operation part is likewise realizable with use of the microcomputer 7 of FIG. 1. Namely, the arithmetic operation part is adapted to have averager means 33 for averaging actual EEG signals Xm (t) segmented, each segment corresponding to a stimulation period T2 in synchronization with an external stimulation signal as shown in FIG. 8. The averager means 33 is connected with the averager means 31 for evaluating the averaged noise signal Zm (k) and with subtractor means 32 for subtracting the averaged noise signal Zm (k) from the EEG signal Ym (t) in FIG. 1.

Figure 9:
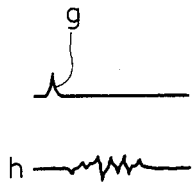

Hereupon, in evaluating the noise signal Zm (k), it is also possible to block a fraction of the stimulation signal (g) and thereafter average the involved EEG signal for improving the accuracy of the estimation of the EKG-originating noise. FIG. 9 depicts an evoked response signal (h) yielded by converting such an averaged signal to an analog signal by means of the D/A converter 9 of FIG. 7.

Furthermore, in obtaining the evoked response, if there is still remained R waves of the EKG in the actual EEG Xm (t), it is possible to block a fraction for a time interval corresponding to 10 ms before and after the trigger pulse (c) and thereafter average the actual EEG signal for improving the estimation accuracy of the evoked response signal.

Although a certain preferred embodiment has been shown and described, it should be understood that many changes and modifications may be made therein without departing from the scope of the appended claims.

What is claimed is:

1. An apparatus for detecting an electroencephalogram comprising:
   (a) an electrode to be attached to the scalp;
   (b) an electrode to be attached to a patient body location other than the scalp;
   (c) an amplifier having input terminals connected with said electrodes for outputting an electroencephalogram (EEG) signal derived between said electrodes;
   (d) trigger generator means for generating a trigger on the basis of R waves involved in an electrocardiogram (EKG) signal;
   (e) averager means for dividing said EEG signal into segments, each corresponding to a period of said EKG signal and starting from a time going back to the past by predetermined time from a time of generating said trigger, and averaging the resultant segmented EEG signals; and
   (f) subtractor means for subtracting an output signal of said averager means from said EEG signal and for thereby generating an actual EEG signal.

2. An apparatus for detecting an electroencephalogram (EEG) according to claim 1, wherein said trigger generator means generates a trigger on the basis of R waves involved in an electrocardiogram detected by other electrodes than the electrodes used to derive an EEG.

3. An apparatus for detecting an electroencephalogram according to claim 1, wherein said trigger generator means generates a trigger on the basis of R waves involved in an electrocardiogram derived from an electroencephalogram.

4. An apparatus for detecting an electroencephalogram according to claim 1, wherein said predetermined time preceding the R waves is set corresponding to time region where P waves are existent.

5. An apparatus for detecting an electroencephalogram according to claim 1, wherein said averager means is adapted to multiply an existing averaged signal by a coefficient $[1-1/m]$ in response to the averaging number $[m]$ and add a value yielded by multiplying a new EEG signal by a coefficient $[1/m]$ to said multiplied value.

6. An apparatus for detecting an electroencephalogram according to claim 5, wherein after said averaging number $[m]$ reaches a predetermined value $[M]$, said coefficients $[1-1/m]$ and $[1/m]$ are fixed respectively to $[1-1/M]$ and $[1/M]$.

7. An apparatus for detecting an evoked response signal comprising:
   (a) an electrode to be attached to the scalp;
   (b) an electrode to be attached to a patient body location other than the scalp;
   (c) an amplifier having input terminals connected with said electrodes for delivering an electroencephalogram (EEG) signal derived between said electrodes;
   (d) trigger generator means for generating a trigger on the basis of R waves involved in an electrocardiogram (EKG) signal;
   (e) first averager means for dividing said EEG signal into segments, each corresponding to a period of said EKG signal and starting from a time going back to the past by a predetermined time from a time of generating said trigger, and for thereby averaging said segmented EEG signals;
   (f) subtractor means for subtracting an output signal of said first averager means from said EEG signal for generating an actual EEG signal; and
   (g) second averager means for dividing said actual EEG signal into segments of said actual signal, each corresponding to a period of a stimulation signal, and averaging such segmented signals in synchronization with said stimulation signal for generating an evoked response signal.

8. An apparatus for detecting an evoked response according to claim 7, wherein said first averager means is adapted to average said segmented EEG signal blocked for a predetermined time before and after a time of generating said stimulation signal.

9. An apparatus for detecting an evoked response signal according to claim 7, wherein said second averager means is adapted to divide said actual EEG signal blocked for a predetermined time before and after a time of generating said trigger in synchronization with said stimulation signal and to thereby average the resultant segmented signals.

* * * * *